United States Patent
Frater-Schröder et al.

(10) Patent No.: US 6,541,042 B1
(45) Date of Patent: Apr. 1, 2003

(54) THERAPEUTICALLY EFFECTIVE COMBINATION

(75) Inventors: Marijke Frater-Schröder, Winterthur (CH); Klemens Brühwiler, Elgg (CH)

(73) Assignee: Bogar AG, Zurich (CH)

( * ) Notice: Subject to any disclaimer, the term of this patent is extended or adjusted under 35 U.S.C. 154(b) by 0 days.

(21) Appl. No.: 09/691,110

(22) Filed: Oct. 19, 2000

(30) Foreign Application Priority Data

Oct. 27, 1999 (CH) ............................................. 1960/99

(51) Int. Cl.$^7$ ............................................. A61K 35/78
(52) U.S. Cl. ....................... 424/725; 424/769; 424/771; 424/773
(58) Field of Search ................................ 424/725, 769, 424/771, 773

(56) References Cited

U.S. PATENT DOCUMENTS

| | | | |
|---|---|---|---|
| 4,877,781 A | * | 10/1989 | LaHaye et al. |
| 5,096,709 A | * | 3/1992 | Vandersloot |
| 5,449,517 A | * | 9/1995 | Fitzjarrell |
| 6,168,794 B1 | * | 1/2001 | Ruesser et al. |
| 2002/0001601 A1 | * | 1/2002 | Dillon et al. |

FOREIGN PATENT DOCUMENTS

| | | | |
|---|---|---|---|
| DE | A 36 40 409 | * | 6/1987 |
| DE | A 196 23 905 | * | 12/1997 |
| EP | A 0 870 507 | * | 10/1998 |
| JP | 03047118 | * | 2/1991 |
| JP | 10298459 | * | 11/1998 |
| WO | WO 99/34811 | * | 7/1999 |

OTHER PUBLICATIONS

Mackenzie, K, The Tea Tree Oil Encyclopedia (1996), Karendon publishing house, pp. 8–10, 25–28, 89–100.*

Blumenthal, M., Therapeutic Guide to Herbal Medicines (1998), American Botanical Council, pp. 194 and 237–241.*

Peirce, A., Practical Guide to Natural Medicine (1999), The Songstone press, pp. 628–631.*

Hagerman, A. 1998. Website reference titled "Biological Activities of Tannins" at http://miavx1.muohoio.edu/—1 page.*

Hagerman, A. 2002. Website titled "Department of Chemistry and Biochemistry Miami University" at http://www-.muohio.edu/—2 pages.*

Website titled "Vegatable Tannis", downloaded 2002, at http:/palimpsest.stanford.edu/don/dt/dt3686.html—3 pages.*

Saller, Von Reinhard et al., "Teebaum–öl: Ein natürliches Universalheilmittel?" *Deutsche Apotheker Zeitung*, 1995; 135; 40–48.*

Buck, David S. et al., "Comparison of Two Topical Preparations for the Treatment of Onychomycosis: *Melaleuca alternifolia*(Tea Tree) Oil and Clotrimazole," *The Journal of Family Practice*, vol. 38, No. 6(Jun.); 1994; 601–605.*

Tong, Melinda M. et al., "Tea Tree Oil in the Treatment of Tinea Pedis," *Australas J. Dermatol*, 1992; 33; 145–149.*

Syed, T.A. et al., "Treatment of toenail onychomycosis with 2% butenafine and 5% *Melaleuca alternifolia* (tea tree) oil in cream," *Tropical Medicine and International Health*, vol. 4, No. 4; 1999; 284–287.*

Ernst, E. et al., "Tea Tree Oil: A Systematic Review of Randomized Clinical Trials," *Forschende Komplementärmedezin*, 2000; 7:17–20.*

Harkenthal, M. et al., "Oxidationsprodukte als mögliche Ursache von Kontaktdermatitiden," *Pharmazie*, 1998; 143; 26–30.*

Gracza, V.L., "Adstringierende Wirkung von Phytopharmaka," *Deutsche Apotheker Zeitung*, No. 44; 1987; 2256–2258.*

* cited by examiner

*Primary Examiner*—Christopher R. Tate
(74) *Attorney, Agent, or Firm*—Oliff & Berridge PLC

(57) ABSTRACT

A therapeutically effective combination comprising 5–25% by weight of terpinen-4-ol-containing essential oils and 0.01 to 10% by weight of tannin-containing medicinal plants or extracts thereof, which is used for the topical treatment of cutaneous and mucous membrane affections in the veterinary sector is described. Used as a terpinen-4-ol-containing essential oil is, in particular, tea tree oil and as a tannin-containing medicinal plant or extract thereof is, in particular, a ratanhia root extract.

10 Claims, No Drawings

THERAPEUTICALLY EFFECTIVE COMBINATION

BACKGROUND OF THE INVENTION

1. Field of Invention

The invention relates to a therapeutically effective combination comprising 5–25% by weight of terpinen-4-ol-containing essential oils and 0.01 to 10% by weight of tannin-containing medicinal plants or extracts or tinctures thereof, which is used for the topical treatment of cutaneous and mucous membrane affections in the veterinary sector.

2. Description of Related Art

Tea tree oil is used in particular according to the invention as terpinen-4-ol-containing essential oils. It is likewise possible to use marjoram oil and marjolaine essence. Examples of tannin-containing medicinal plants used are ratanhia root (ratanhiae radix), in particular a ratanhia root extract. Particularly preferred medicinal plants are uvae ursi folium, Quercus cortex, Thea nigra, tormentillae radix, Hamamelis folium, ratanhiae radix, Hamamelis cortex, Orthosiphonis folium and Juglandis folium. Tea tree oil (*Melaleucae aetheroleum*) is the essential oil obtained by steam distillation from the leaves and twig tips of *Melaleucae alternifolia* Cheel, *Melaleucae linariifolia* Sm., *Melaleucae dissitiflora* Mueller or other species of the genus Melaleucae (Myrtaceae).

The synergistic combination according to the invention comprises 5–25% by weight, preferably 10% by weight, of terpinen-4-ol-containing essential oils, and 0.01 to 10% by weight, preferably 0.1 to 2% by weight, of tannin-containing medicinal plants or extracts or tinctures thereof, the extracts or tinctures preferably containing 0.1 to 2% by weight of the herbal drug. Ratanhia root extract is particularly preferred. Ratanhia root extract contains not less than 5% by weight of tannins expressed as pyrogallol. At these doses, the combination according to the invention shows no toxic reactions.

The tea tree oil used in particular as an ingredient in the combination according to the invention is known (see, for example, DE-A 196 23 905), and its therapeutic effect is described in many places in the literature. It contains besides at least 30% by weight of terpinen-4-ol also a maximum of 15% by weight of 1,8-cineol and, in addition, cymene, pinene, terpineol, α-terpinene, limonene, α-terpineol, γ-terpinene. The ratanhia root extracts which are also used in particular as ingredients in the combination according to the invention are likewise known, and their therapeutic effect is described in many places in the literature.

EP 0 870 507 A1 shows that preparations containing 0.02 to 5% by weight of an essential oil, and 1 to 10% by weight of an herbal extract whose content is undefined have a synergistic antimicrobial effect in vitro, no specific target organ being indicated apart from the mouth. Tea tree oil inter alia is used as essential oil in the preparation. WO 99/34811 by the same inventors shows that preparations containing 0.1 to 5% by weight of an essential oil, and 1 to 10% by weight of an herbal extract whose content is undefined display an antimycotic effect in vitro. The preparations used in some of these cases have a composition identical to the preparations described in 0 870 507 A1. It was possible to show in the more recent publication (WO 99/34811) at most an additive effect, tending to be restricted just to the essential oil, but not a synergistic effect. A fundamental problem in the use of antimycotic preparations is their lack of activity for mixed infections, which has disadvantageous consequences because most infections are mixed infections.

It is disclosed in the Deutsche Apothekerzeitung, 1995, 135, 40–48, that tea tree oil is used in dermatological and stomatological products, for example shampoos, hand and body creams and lotions. The Journal of Family Practice, vol. 38, no. 6 (June), 1994, describes the in vivo treatment of patients suffering from onychomycosis with 100% tea tree oil. In these cases it was possible to achieve only moderate success; in particular, a high rate of recurrence was recorded. In an in vivo comparison of 10% by weight tea tree oil cream with 1% by weight tolnaftate for the treatment of patients with manifestations caused by tinea pedis, however, it emerged that tea tree oil on its own has a very weak or no antimycotic effect, equivalent to that of placebo (in this connection, see Austral. J. Dermatol. 1992; 33: 145–149). In a new in vivo study, which is described in Tropical Medicine and International Health (1999; 4; 284–287), a 5% by weight tea tree oil-containing cream was compared with a cream containing 5% by weight of tea tree oil and 2% of butenafine hydrochloride in the treatment of patients suffering from onychomycosis. In this case no effect was achievable on treatment with cream containing only tea tree oil.

In summary, recent literature shows that the results of the clinical studies carried out to date with preparations containing tea tree oil are not as convincing in vivo as are the in vitro experiments described in the older literature (see, for example, Forsch. Komplementärmed. 2000, 7:17–20).

In addition, skin irritation and allergic reactions are frequently observed on use of skin care and cosmetic products containing tea tree oil. It has been shown in Pharmazie, 1998, 143, 26–30, that these allergic reactions and skin irritation are primarily attributable to oxidation products resulting from autoxidation of the essential oil on storage.

Concerning the tannin-containing ratanhia root extract it was known, inter alia, (see, for example, Deutsche Apotheker Zeitung 127, vol. no. 44, pages 2256–2258 of Oct. 29, 1987), that, owing to its astringent effect, the latter is able to reduce the permeability of tissues, to increase the mechanical resistance of tissues, to impede the absorbability of toxic substances, to stop capillary hemorrhages and to achieve a mild antimicrobial effect. It was also known to employ ratanhia root extracts for bacterial infections and fungal infections of the skin (see, for example, DE-A 364 04 09 of Sato Pharm. Co.). It was furthermore known that tannin-containing herbal drugs display an antioxidant effect and have radical scavenger properties.

SUMMARY OF THE INVENTION

It has now been found according to the invention that a therapeutically effective aqueous combination comprising 5 to 25% by weight of terpinen-4-ol-containing essential oils and 0.01–10% by weight of tannin-containing medicinal plants or extracts thereof has surprisingly been shown in a clinical study to achieve a synergistic effect in the area of chronic dermatitis in animals on in vivo treatment of cutaneous and mucous membrane affections, i.e. mixed infections, which results in an extremely good curative effect on topical use in the veterinary sector. On the basis of this synergistic effect, the combination according to the invention proves to have antimycotic, antibacterial, antiinflammatory and antiviral activity for cutaneous and mucous membrane affections and can moreover be employed for wound healing. It is likewise effective for nonspecific eczema, for allergic dermatitis, for fleabite allergy, for interdigital pyoderma, lick dermatitis and skinfold pyoderma of dogs and cats. On the basis of these effects it is possible to use the combination according to the invention inter alia for the treatment of pathological signs such as, for example, itching (pruritus), reddening (erythema), erosion, of papules, pustules, weeping surfaces, pus, crusts, hair loss (alopecia), skin thickening, urticaria, scaling, hyperpigmentation and vesicles, but also of incision wounds and abrasions, viral infections, bacterial and fungal infections, of infections in the urogentital region, ulcers and furuncles, but also of allergies and other skin problems, for example those resulting by overbreeding.

Surprisingly, the synergistic therapeutic effect of the combination according to the invention also extends in particular to mixed infections of the aforementioned type. This means that the novel therapeutically effective combination according to the invention represents a surprisingly effective and welcome alternative to the antibiotics and/or cortisone therapies customary to date.

The surprisingly good in vivo effect of the combination according to the invention presumably also derives from the fact that, for example, microorganisms are attacked and killed by the ingredients of the combination through at least two points of attack, the effect having a superadditive, i.e. synergistic, onset. The antimycotic effect of the combination in vivo is likewise surprising and was not to be expected on the basis of the virtual lack of activity, discussed above, of tea tree oil on its own in vivo on treatment of tinea pedis. The surprisingly good antiviral effect of the combination according to the invention is presumably associated with a clumping and thus inactivation of viral particles.

The use for animal therapy can take place for a large number of genera with similar skin characteristics. Particularly to be emphasized in this connection are mammals such as dogs, cats and horses (so-called companion animals), feathered species such as birds and fowls, agricultural livestock such as cows, pigs and rabbits. Hairy animals are particularly important in this connection.

The combination according to the invention also shows a good effect on topical treatment of cutaneous and mucous membrane affections in humans.

DETAILED DESCRIPTION OF PREFERRED EMBODIMENTS

The production of terpinen-4-ol-containing preparations having high storage stability is exceptionally demanding. With the preparation according to the invention it has been possible to achieve through the addition of a tannin-containing herbal extract not just a synergistic effect. It has also emerged that, for example, ratanhia extract inhibits the autooxidation of terpinen-4-ol. Thus the preparation according to the invention has exceptionally high storage stability and is moreover very well tolerated.

In a preferred embodiment, the preparation according to the invention has a high water content. An auxiliary is required to stabilize such an emulsion with a high essential oil content over a prolonged period because, otherwise, segregation of the oily and aqueous phases occurs. Such a segregation is prevented in the preparation according to the invention through addition of 5-ureidohydantoin. Topical use of the combination according to the invention can take place in all possible topical use forms, for example as emulsions, creams, ointments, gels or liquids such as, for example, oils or tinctures, which, besides the ingredients detailed above in the combination according to the invention, also contain the additions customary in pharmaceutical preparations.

EXAMPLES

The following examples serve to illustrate the invention without restricting its scope.

Example 1

Formula for a (Creamy) Emulsion
Active Ingredients:
  10% by weight essential oil from the tea tree
  1% by weight ratanhia root extract tincture (1:2)
Excipients:
  almond oil
  lanolin
  cetyl alcohol
  emulsifiers, stearic acid and triethanolamine
  aqueous phase 69%

Example 2

Formula for a (Creamy) Emulsion
Active Ingredients:
  10% by weight essential oil from the tea tree
  0.05% by weight ratanhia root extract siccum (5:1)
Excipients:
  almond oil
  lanolin
  cetyl alcohol
  emulsifiers, stearic acid and triethanolamine
  aqueous phase 69%

Example 3

Formula for a (Creamy) Emulsion
Active Ingredients:
  10% by weight essential oil from marjoram
  1% by weight ratanhia root extract tincture (1:2)
Excipients:
  almond oil
  lanolin
  celtyl alcohol
  emulsifiers, stearic acid and triethanolamine
  aqueous phase 69%

Example 4

Formula for a (Creamy) Emulsion
Active Ingredients:
  10% by weight essential oil from the tea tree
  1% oak bark (Quercus cortex) in extract form
Excipients:
  almond oil
  lanolin
  cetyl alcohol
  emulsifiers, stearic acid and triethanolamine
  aqueous phase 69%

Example 5

Formula for a (Creamy) Emulsion
Active Ingredients:
  15% by weight essential oil from the tea tree
  2% tormentillae radix in extract form
Excipients:
  almond oil
  lanolin
  cetyl alcohol
  emulsifiers, stearic acid and triethanolamine
  aqueous phase 69%

Example 6

Formula for a (Creamy) Emulsion

Active Ingredients:
  10% by weight essential oil from marjoram
  1% by weight hamamelidis cortex in extract form Excipients:
  almond oil
  lanolin
  cetyl alcohol
  emulsifiers, stearic acid and triethanolamine
  aqueous phase 69%

Example 7

Clinical Study

This study was an open, multi-center study on the efficacy and safety of DERMA-PHYTONIKUM in dogs and cats for the treatment of chronic and/or allergic dermatitis with or without pruritus, comparing the degree of severity at the beginning and end of the study.

An open multicentered, controlled clinical trial was conducted to confirm the efficacy and safety of the DERMA-PHYTONIKUM cream (described in Example 2) in the treatment of chronic dermatitis in dogs and cats. The study was performed in compliance with the "International Cooperation on Harmonization of Technical Requirements for Registration of Veterinary Medicinal Products (VICH) Topic GL 9", and the "Guideline on Good Clinical Practices (December 1998)".

Animals were selected, with written informed owner consent, by fourteen investigators who were practicing veterinarians in Switzerland. Selection was based upon compatibility with inclusion/exclusion criteria and examination of the animal as detailed in the study protocol. The veterinary investigator clinically examined animals on the first visit (Table 1).

TABLE 1

Incidence of Dermatitis in Dogs and Cats

| Clinical Conditions of Dermatitis | Dogs (n = 53) | Cats (n = 19) |
| --- | --- | --- |
| Non-specific eczema | 30 (56.6%) | 15 (78.9%) |
| Allergic dermatitis | 15 (28.3%) | 3 (15.8%) |
| Flea allergy dermatitis | 2 (3.8%) | 1 (5.3%) |
| Contact dermatitis | 3 (5.7%) | 3 (15.8%) |
| Eosinophilic granuloma complex in the cat | 0 | 2 (10.5%) |
| Interdigital pyoderma | 5 (9.4%) | 0 |
| Lick Dermatitis | 21 (39.6%) | 5 (26.3%) |
| Skinfold pyoderma | 4 (7.5%) | 0 |

Details of symptoms and severity of symptoms were described and recorded. Size and site of lesion(s), diagnosis and cause of the dermnatitis (if known), were also recorded. The pet owner applied the DERMA-PHYTONIKUM creamn thinly to the lesion(s) twice daily for a period of 28 days. This was recorded by the owner in a 'Pet owner diary', together with an assessment of the progression of the condition as 'better', 'unchanged' or 'worse'. Two optional repeat visits could be made to the investigator during the 28 day treatment period. The investigator performed a final examination after the end of treatment. All adverse events were recorded. Following medications were excluded during the study: corticosteroids, antibiotics and phytomedicines. The investigator made an evaluation of efficacy at each interim visit and after 28 days of treatment for each animal.

Efficacy was assessed by considering the degree of severity of the symptoms of pruritus, erythema, erosion, papules, pustules, oozing surface, pus, scabs, alopecia, skin thickening, urticaria, scaliness, hyperpigmentation and vesicles as recorded before and after treatment with DERMA-PHYTONIKUM.

The investigator made an overall evaluation of efficacy after the end of treatment at the final visit and this was recorded as 'very good', 'good', 'moderate', or 'unsatisfactory'.

The investigator made an assessment of overall tolerability of the treatment for each animal by considering the frequency and nature of any adverse events. Tolerability was recorded as 'very good', 'good', 'moderate', or 'unsatisfactory'.

Results of Efficacy in Dogs and Cats

Seventy-two (72) animals, 53 dogs and 19 cats were enrolled in the study. Animals with chronic conditions were incorporated into the study. In this "steady state" situation each animal was evaluated as its own control. Three dogs and three cats discontinued the study due to adverse events. Only two were due to the application of DERMA-PHYTONIKUM as described in the study protocol. Four dogs and one cat discontinued the study for other reasons. All recorded data was analyzed.

Data from all animals that received the study medication was analyzed, using version 6.12 of the SAS statistical package. Statistical analysis of efficacy showed that 82% (42/51) (evaluation not available for 2 dogs) of dogs with chronic dermatitis treated with DERMA-PHYTONIKUM had a 'good' or 'very good' response to treatment, significant at the 5% level with a 95% confidence interval of 72% to 92% (Table 2).

Eighty four (84)% (16/19) of cats with chronic dermatitis treated with DERMA-PHYTONIKUM had a 'good' or 'very good' response to treatment, with a 95% confidence interval of 68% to 100% (Table 2).

TABLE 2

Summary of Primary Efficacy Results for Dogs and Cats

| | Global Efficacy after Derma-Phytonikum treatment | | |
| --- | --- | --- | --- |
| Species | Very Good/Good | Moderate | Unsatisfactory |
| Dogs (n = 51*) | 42 (82%) | 4 (7.8%) | 5 (9.8%) |
| Cats (n = 19*) | 16 (84%) | 2* (10.5%) | 1 (5.3%) |

*Original CRF not completed for global efficacy for 2 dogs

Between the first visit, before treatment and the 4th visit at the end of 4 weeks treatment both reduction of symptoms and significant reduction of severity of symptoms was observed in dogs.

Treatment with DERMA-PHYTONIKUM significantly reduced (Bowkers statistic) symptoms of pruritus, erythema, erosion, oozing surface, scabs, alopecia, skin thickening and scaliness in dogs (Tables 3 and 4).

TABLE 3

Treatment with Derma-Phytonikum: Incidence of clinical symptoms in dogs before treatment, at day 15 (+/− 3 days) and after 4 weeks of treatment

| Clinical Symptoms of dermatitis in dogs | Visit 1 Before treatment (n = 53) % | Visit 2 During treatment (n = 30) % | Visit 4 After 28 days of treatment (n = 47) % |
|---|---|---|---|
| Pruritus | 96.2 | 88.6 | 27.7 |
| Erythema | 88.7 | 68.6 | 21.3 |
| Erosion | 58.5 | 45.7 | 6.4 |
| Papules | 20.8 | 14.3 | 2.1 |
| Pustules | 30.2 | 20.0 | 2.1 |
| Oozing Surface | 66.0 | 34.3 | 6.4 |
| Pus | 35.8 | 17.1 | 2.1 |
| Scabs | 50.9 | 51.4 | 21.3 |
| Alopecia | 73.6 | 57.1 | 38.3 |
| Skin Thickening | 58.5 | 40.0 | 23.4 |
| Urticaria | 5.7 | 0.00 | 2.1 |
| Scaliness | 50.9 | 57.1 | 34.0 |
| Hyper-pigmentation | 18.9 | 11.4 | 19.1 |
| Vesicles | 3.8 | 2.9 | 0.00 | n = number of dogs

TABLE 4

Reduction in severity of symptoms in dogs after 4 weeks of treatment with Derma-Phytonikum

| Clinical Symptoms of dermatitis in dogs | Bowker's Statistic Visit 1:Visit 4 Significance YES | NO |
|---|---|---|
| Pruritus | 43.0 | |
| Erythema | 36.7 | |
| Erosion | 27.0 | |
| Papules | | 10.0 |
| Pustules | 14.0 | |
| Oozing Surface | 31.0 | |
| Pus | 17.0 | |
| Scabs | 20.3 | |
| Alopecia | 31.0 | |
| Skin Thickening | 24.0 | |
| Urticaria | | 2.0 |
| Scaliness | 16.6 | |
| Hyper-pigmentation | | 2.5 |
| Vesicles | | 2.0 |

A statistically significant improvement as well as a significant reduction in number of symptoms was achieved between visit 1, before treatment and visit 4, after 4 weeks of treatment.

Treatment with DERMA-PHYTONIKUM significantly reduced severity of symptoms (Bowkers statistic) of pruritus and scabs in cats (Tables 5,6).

TABLE 5

Treatment with Derma-Phytonikum: Incidence of clinical symptoms in cats before treatment (visit 1), day 15 (+/− 3 days) (visit 2) and after 4 weeks of treatment. (visit 4)

| Clinical Symptoms of dermatitis in cats | Visit 1 Before treatment n = 19 % | Study day 15 (+/− 3 days) during treatment n = 12 % | Visit 4 After treatment n = 16 % |
|---|---|---|---|
| Pruritus | 100.0 | 92.3 | 12.5 |
| Erythema | 68.4 | 76.9 | 18.8 |
| Erosion | 78.9 | 76.9 | 12.5 |
| Papules | 5.3 | 0.00 | 6.3 |
| Pustules | 15.8 | 7.7 | 0.00 |
| Oozing Surface | 68.4 | 23.1 | 12.5 |
| Pus | 5.3 | 0.00 | 0.00 |
| Scabs | 94.7 | 76.9 | 25.0 |
| Alopecia | 94.7 | 53.8 | 43.8 |
| Skin Thickening | 21.1 | 15.4 | 6.3 |
| Urticaria | 0.00 | 0.00 | 0.00 |
| Scaliness | 63.2 | 53.8 | 12.5 |
| Hyper-pigmentation | 0.00 | 0.00 | 0.00 |
| Vesicles | 5.3 | 0.00 | 0.00 | n = number of cats

TABLE 6

Reduction in severity of symptoms in cats after 4 weeks of treatment with Derma-Phytonikum

| Clinical Symptoms of dermatitis in cats | Bowker's Statistic Visit 1:Visit 4 Significance YES | NO |
|---|---|---|
| Pruritus | 16.0 | |
| Erythema | | 11.0 |
| Erosion | | 11.0 |
| Papules | | 1.0 |
| Pustules | | 3.0 |
| Oozing Surface | | 8.8 |
| Pus | | 1.0 |
| Scabs | 14.0 | |
| Alopecia | | 11.7 |
| Skin Thickening | | 2.3 |
| Scaliness | | 10.0 |
| Hyper-pigmentation | — | — |
| Vesicles | | 1.0 |

Results of Safety Evaluation

Primary evaluation of safety was based on the occurrence of adverse events and their nature.

Eighty five (85)% (44/52) of dogs were judged to have an overall tolerability of 'good' or 'very good', significant at the 5% level with a 95% confidence interval of 75% to 95% (Table 7).

Eighty four (84)% (16/19) of cats were judged to have an overall tolerability of 'good' or 'very good', with a 95% confidence interval of 68% to 100%. The wide confidence interval reflects the small sample size for cats in this study (Table 7).

TABLE 7

Summary of Overall Evaluation
of Safety Results in Dogs and Cats

Global Tolerability
after Derma-Phytonikum Treatment

| Species | Very Good/Good | Moderate | Unsatisfactory |
|---|---|---|---|
| Dogs (n = 52)* | 44 (85%) | 7 (13.5%) | 1 (1.9%) |
| Cats (n = 19) | 16 (84%) | 2 (10.5%) | 1 (5.3%) |

*Original CRF not completed for overall evaluation of safety for 1 dog

Following evaluation of the data only two dogs (2/53) had an adverse event probably resulting from the application of DERMA-PHYTONIKUM. In both dogs reversible localized irritation and hyperaemia were observed after interdigital application.

Three cats (3/19) had adverse events probably resulting from the application of DERMA-PHYTONIKUM. In all three cats treatment was applied to the ear base (between the eye and the entrance to the outer ear) and localized, reversible reactions at the treatment site were recorded.

General Conclusion Concerning Efficacy and Safety
of Derma-Phytonikum

This controlled study performed in veterinary practices in Switzerland has shown that the topical application of DERMA-PHYTONIKUM twice daily for 28 consecutive days is safe and efficacious for the treatment of chronic and/or allergic dermatitis in dogs and cats.

What is claimed is:

1. A therapeutically effective aqueous emulsion comprising (i) 10 to 25% by weight of one or more terpinen-4-ol-containing essential oils and (ii) 0.01–10% by weight of one or more tannin-containing medicinal plants selected from the group consisting of ratanhia root, uvae ursi folium, Hamamelis cortex, Orthosiphonis folium, Juglandis folium, extracts thereof and tinctures thereof, for the topical treatment of cutaneous and mucous membrane afflictions, the emulsion being stable in storage.

2. The emulsion of claim 1, comprising 0.1–2% by weight of the extract or tincture of the tannin-containing medicinal plants.

3. The emulsion of claim 1, wherein the essential oil comprises at least 20% terpinen-4-ol.

4. The emulsion of claim 1, wherein the terpinen-4-ol-containing essential oil is tea tree oil.

5. The emulsion of claim 1, wherein at least 2% tannins are present in the tannin-containing medicinal plants.

6. The emulsion of claim 1, wherein the tannin-containing medicinal plant or extract thereof is a ratanhia root extract.

7. The emulsion of claim 1, which is in a topical use form.

8. The emulsion of claim 7, wherein said topical use form is a cream, ointment, gel, oil or tincture.

9. A composition for the topical treatment of cutaneous and mucous membrane affections comprising the emulsion of claim 1.

10. A derma-phytonikum comprising a therapeutically effective aqueous emulsion comprising (i) 10 to 25% by weight of one or more terpinen-4-ol-containing essential oils and (ii) 0.01–10% by weight of one or more tannin-containing medicinal plants selected from the group consisting of ratanhia root, uvae ursi folium, Hamamelis cortex, Orthosiphonis folium, Juglandis folium, extracts thereof and tinctures thereof for the topical treatment of cutaneous and mucous membrane afflictions in the veterinary sector, the emulsion being stable in storage.

* * * * *